(12) United States Patent
Davis et al.

(10) Patent No.: US 10,893,711 B1
(45) Date of Patent: Jan. 19, 2021

(54) COOLING OR HEATING NECKBAND

(71) Applicants: George Davis, Welford, SC (US);
Roger Suddeth, Welford, SC (US)

(72) Inventors: George Davis, Welford, SC (US);
Roger Suddeth, Welford, SC (US)

( * ) Notice: Subject to any disclaimer, the term of this patent is extended or adjusted under 35 U.S.C. 154(b) by 225 days.

(21) Appl. No.: 15/985,888

(22) Filed: May 22, 2018

(51) Int. Cl.
| | | |
|---|---|---|
| *A41D 13/005* | (2006.01) | |
| *A41D 20/00* | (2006.01) | |
| *A61F 7/02* | (2006.01) | |
| *A61F 7/10* | (2006.01) | |
| *A41D 23/00* | (2006.01) | |
| *A61F 7/00* | (2006.01) | |

(52) U.S. Cl.
CPC .............. *A41D 20/005* (2013.01); *A61F 7/02* (2013.01); *A61F 7/10* (2013.01); *A41D 2023/002* (2013.01); *A61F 2007/0007* (2013.01); *A61F 2007/0009* (2013.01)

(58) Field of Classification Search
CPC ............ A41D 13/0053; A41D 13/0055; A41D 13/0056; A41D 13/0058
See application file for complete search history.

(56) References Cited

U.S. PATENT DOCUMENTS

| | | | |
|---|---|---|---|
| 4,326,533 A * | 4/1982 | Henderson | ................ F25D 3/08 2/171.2 |
| 4,641,655 A | 2/1987 | Abt | |
| 4,805,619 A | 2/1989 | Swearingen | |
| 5,265,669 A | 11/1993 | Schneider | |
| 5,295,949 A | 3/1994 | Hathaway | |
| 5,507,793 A | 4/1996 | Hodges | |
| 5,802,865 A * | 9/1998 | Strauss | ............... A41D 13/0025 62/259.3 |
| 6,564,390 B2 * | 5/2003 | Vernon | ................... A41D 20/00 2/171 |
| D555,836 S | 11/2007 | Foust | |
| 8,292,936 B2 | 10/2012 | Jung | |
| 2005/0177925 A1 | 8/2005 | Peeples | |
| 2007/0213794 A1 | 9/2007 | Lauver | |
| 2008/0289351 A1 * | 11/2008 | Taylor | ........................ A61F 7/10 62/259.3 |
| 2016/0338427 A1 * | 11/2016 | Hsiao | ..................... F24F 5/0042 |
| 2017/0087007 A1 * | 3/2017 | Yang | .......................... A61F 7/02 |

* cited by examiner

*Primary Examiner* — Brian M King (57) ABSTRACT

The cooling and heating neckband is adapted for use with a person. The person is further defined with a head and a neck. The cooling and heating neckband is worn by the person. The cooling and heating neckband transfers heat to and from the person to make the person more comfortable. The cooling and heating neckband comprises a heat transfer structure, a foam layer, and a covering structure. The heat transfer structure is an apparatus that transfers heat to and from the person during physical activity. The foam layer is a cushion that covers the heat transfer structure. The covering structure is a textile-based structure. The heat transfer structure and the foam layer are inserted in the covering structure. The covering structure attaches the cooling and heating neckband to the person.

18 Claims, 5 Drawing Sheets

COOLING OR HEATING NECKBAND

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of personal and domestic articles including wearing apparel, more specifically, a scarf with a cooling effect.

SUMMARY OF INVENTION

The cooling and heating neckband is adapted for use with a person. The person is further defined with a head and a neck. The cooling and heating neckband is worn by the person. The cooling and heating neckband transfers heat to and from the person to make the person more comfortable. The cooling and heating neckband comprises a heat transfer structure, a foam layer, and a covering structure. The heat transfer structure is an apparatus that transfers heat to and from the person during physical activity. The foam layer is a cushion that covers the heat transfer structure. The covering structure is a textile-based structure. The heat transfer structure and the foam layer are inserted in the covering structure. The covering structure attaches the cooling and heating neckband to the person.

These together with additional objects, features and advantages of the cooling and heating neckband will be readily apparent to those of ordinary skill in the art upon reading the following detailed description of the presently preferred, but nonetheless illustrative, embodiments when taken in conjunction with the accompanying drawings.

In this respect, before explaining the current embodiments of the cooling and heating neckband in detail, it is to be understood that the cooling and heating neckband is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the cooling and heating neckband.

It is therefore important that the claims be regarded as including such equivalent construction insofar as they do not depart from the spirit and scope of the cooling and heating neckband. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to one or more potential embodiments of the disclosure, which are illustrated in FIGS. 1 through 6.

The cooling and heating neckband 100 (hereinafter invention) is adapted for use with a person 161. The person 161 is further defined with a head 162 and a neck 163. The invention 100 is worn by the person 161. The invention 100 transfers heat to and from the person 161 to make the person 161 more comfortable. The invention 100 comprises a heat transfer structure 101, a foam layer 102, and a covering structure 103. The heat transfer structure 101 is an apparatus that transfers heat to and from the person 161 during physical activity. The foam layer 102 is a cushion that covers the heat transfer structure 101. The covering structure 103 is a textile-based structure. The heat transfer structure 101 and the foam layer 102 are inserted in the covering structure 103. The covering structure 103 attaches the invention 100 to the person 161.

The heat transfer structure 101 is an insulated structure. The heat transfer structure 101 is a hollow horseshoe-shaped structure. The heat transfer structure 101 is sized to fit on a location selected from the group consisting of the head 162 of the person 161 and the neck 163 of the person 161. The heat transfer structure 101 is worn during physical activity. The heat transfer structure 101 contains a heat transfer medium 125 that is used to transfer heat between the person 161 and the invention 100.

The heat transfer structure 101 is configured to perform a function selected from the group consisting of: 1) cooling the person 161 by drawing heat away from the person 161 into the heat transfer structure 101; and, 2) warming the person 161 by allowing the person 161 to draw heat from the heat transfer structure 101.

The heat transfer structure 101 acts as a spring. Specifically, when the ends of the heat transfer structure 101 are separated to allow the head 162 of the person 161 to fit within the invention 100, the heat transfer structure 101 is deformed such that the heat transfer structure 101: 1) resists the application of the force that separates the ends; and 2) stores the deformation energy such that when the force is no longer applied the heat transfer structure 101 returns to its relaxed shape. In this circumstance, the head 162 will prevent the heat transfer structure 101 from returning to its relaxed shape. The heat transfer structure 101 will apply a force against the head 162 that binds the heat transfer structure 101 to the head 162.

The heat transfer structure 101 comprises a shell 111, a reservoir 112, a joint 113, and a negative buffer 114. The shell 111 is further defined with a shell inner perimeter 141 and a shell outer perimeter 142. The reservoir 112 is further defined with a reservoir inner perimeter 143 and a reservoir outer perimeter 144. The shell inner perimeter 141 refers to the inner perimeter of the horseshoe structure of the shell 111. The shell outer perimeter 142 refers to the outer perimeter of the horseshoe structure of the shell 111. The reservoir inner perimeter 143 refers to the inner perimeter of the horseshoe structure of the reservoir 112. The reservoir outer perimeter 144 refers to the outer perimeter of the horseshoe structure of the reservoir 112. The inner and outer perimeters of a structure are described in greater detail elsewhere in this disclosure.

The shell 111 is a hollow semi-rigid structure. The semi-rigid structure of the shell 111 has an elastic nature. The shell 111 forms the exterior surface of the heat transfer structure 101. The shell 111 has a horseshoe shape. The shell 111 is formed from aluminum. The applicant prefers aluminum because of it has good structural strength with a reasonably low specific heat capacity that allows it to transfer heat readily. The shell 111 the hollow interior of the shell 111 is a gas impermeable structure capable of maintaining the gas at the reduced pressures of a vacuum. The shell 111 contains the reservoir 112 such that the reservoir 112 is primarily contained within shell 111. The shell 111 contains the reservoir 112 such that the reservoir 112 is located within the reduced pressure environment of the shell 111.

The reservoir 112 is a hollow semi-rigid structure. The semi-rigid structure of the reservoir 112 has an elastic nature. The reservoir 112 forms a fluid impermeable space within the interior of the shell 111. The reservoir 112 contains the heat transfer medium 125. The reservoir 112 is geometrically similar to the shell 111. The reservoir inner perimeter 143 of the reservoir 112 is directly joined to the shell inner perimeter 141 of the shell 111 such that heat can transfer between the shell 111 and the heat transfer medium 125 contained within the reservoir 112. The reservoir 112 is a gas impermeable structure that contains the heat transfer medium 125 at a pressure that is different from the low-pressure gas contained within the shell 111. The reservoir 112 is formed from bronze. The applicant prefers bronze because its low specific heat capacity makes it exceptionally efficient at heat transfer. The reservoir 112 further comprises a chamber 121, a port 122, a cap 123, and a threaded connection 124.

The hollow interior of the reservoir 112 forms the chamber 121. The chamber 121 forms the storage space within which the heat transfer medium 125 is stored. The chamber 121 is a fluid impermeable enclosed structure. The port 122 is a tubular structure that provides access to the chamber 121. The heat transfer medium 125 is introduced into and removed from the chamber 121 through the port 122.

The port 122 projects away from the chamber 121 in a direction towards the shell outer perimeter 142 of the shell 111. The shell 111 forms a brazed seal around the port 122 as it passes through the shell outer perimeter 142. The cap 123 is a closure placed over the open end of the port 122. The use of a cap 123 is well-known and documented in society. The threaded connection 124 attaches the cap 123 to the open end of the port 122. The threaded connection 124 is discussed in greater detail elsewhere in this disclosure.

The heat transfer medium 125 is a fluid that is heated or cooled before being introduced into the chamber 121. The temperature of the heat transfer medium 125 determines the direction of heat transfer during use of the invention 100. In the first potential embodiment of the disclosure, the applicant prefers that the specific heat capacity of the selected heat transfer medium 125 be greater than or equal the specific heat capacity of water.

The joint 113 is a flux material that is used to braze the reservoir inner perimeter 143 to the shell inner perimeter 141. Methods to form a brazed or welded joint 113 that attaches bronze to aluminum are well-known and documented in the mechanical arts.

The negative buffer 114 is a negative space formed between the shell outer perimeter 142 of the shell 111 and the reservoir outer perimeter 144 of the reservoir 112. The reduced pressure gas is stored in the negative buffer 114. The reduced pressure gas in the negative buffer 114 forms an insulating structure that inhibits heat transfer in a direction away from the person 161 wearing the invention 100.

The foam layer 102 is a cushion. The foam layer 102 attaches to the exterior surfaces of the heat transfer structure 101. The foam layer 102 prevents injury to the person 161 from the heat transfer structure 101. In the first potential embodiment of the disclosure, the foam layer 102 is a polyurethane foam. The covering structure 103 is a tubular textile.

The foam layer 102 further comprises an inner cap aperture 131. The inner cap aperture 131 is an aperture formed through the foam layer 102. The inner cap aperture 131 allows the port 122 to pass through the foam layer 102.

The heat transfer structure 101 and the foam layer 102 are inserted into the covering structure 103. The covering structure 103 is a wicking structure that draws perspiration away from the person 161 during physical activity. In the first potential embodiment of the disclosure assumes that the covering structure 103 is an elastic textile that is fitted over the port 122. The span of the center axis of the covering structure 103 is greater than the span of the shell outer perimeter 142 of the heat transfer structure 101 such that the ends of the covering structure 103 can be tied together to secure the invention 100 to the person 161.

The covering structure 103 acts as a spring. Specifically, when the heat transfer structure 101 and foam layer 102 are inserted into the covering structure 103, a radial force is applied to the covering structure 103 in a direction perpendicular to the center axis of the covering structure 103. The applied radial force elongates the span of the diameter the covering structure 103 in the direction perpendicular to the center axis of the covering structure 103. The elasticity of the covering structure 103 creates a force that opposes the displacement created by the applied force. The elasticity of the covering structure 103 returns the covering structure 103 to its relaxed shape. The heat transfer structure 101 and foam layer 102 will prevent the covering structure 103 from returning to its relaxed shape. In this circumstance, the covering structure 103 will apply a force projecting radially towards the center axis of the covering structure 103 that binds the covering structure 103 to the heat transfer structure 101 and foam layer 102.

The covering structure 103 further comprises an outer cap aperture 132. The outer cap aperture 132 is an aperture formed through the covering structure 103. The outer cap aperture 132 allows the port 122 to pass through the covering structure 103.

Figure 1:
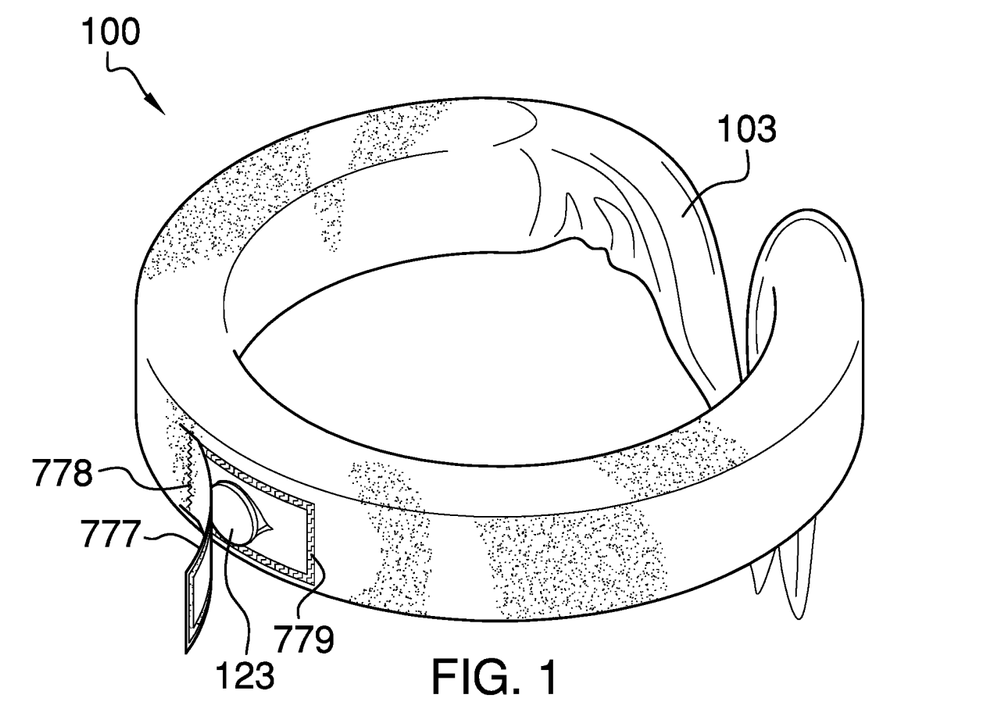
FIG. 1 is a perspective view of an embodiment of the disclosure.
Figure 2:
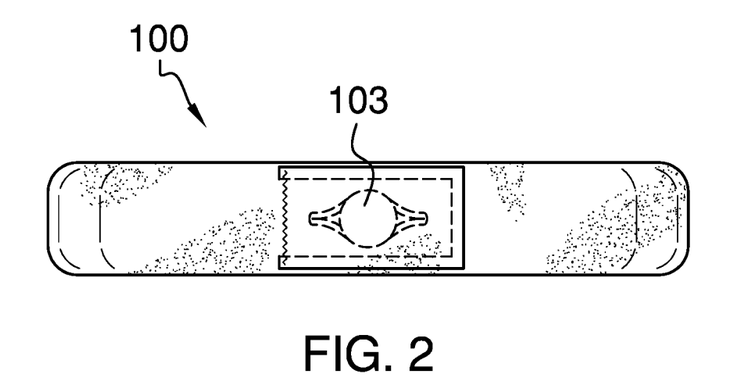
FIG. 2 is a front view of an embodiment of the disclosure.
Figure 3:
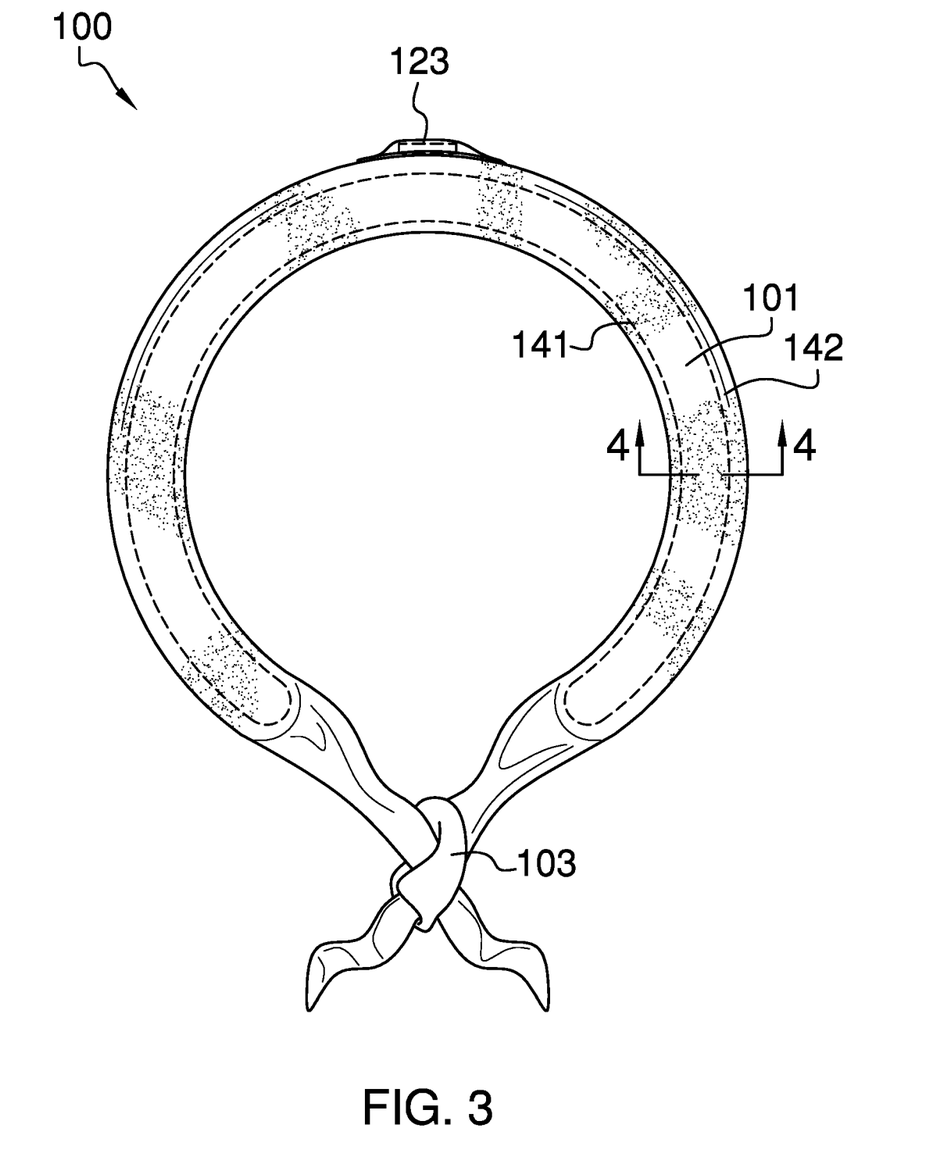
FIG. 3 is a top view of an embodiment of the disclosure.
Figure 4:
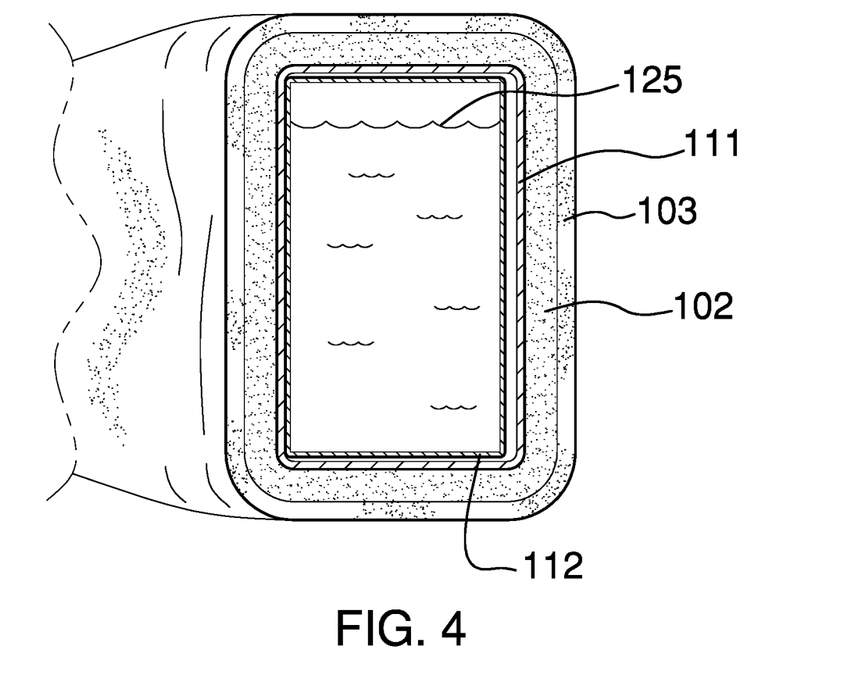
FIG. 4 is a cross-sectional view of an embodiment of the disclosure across 4-4 as shown in FIG. 3.
Figure 5:
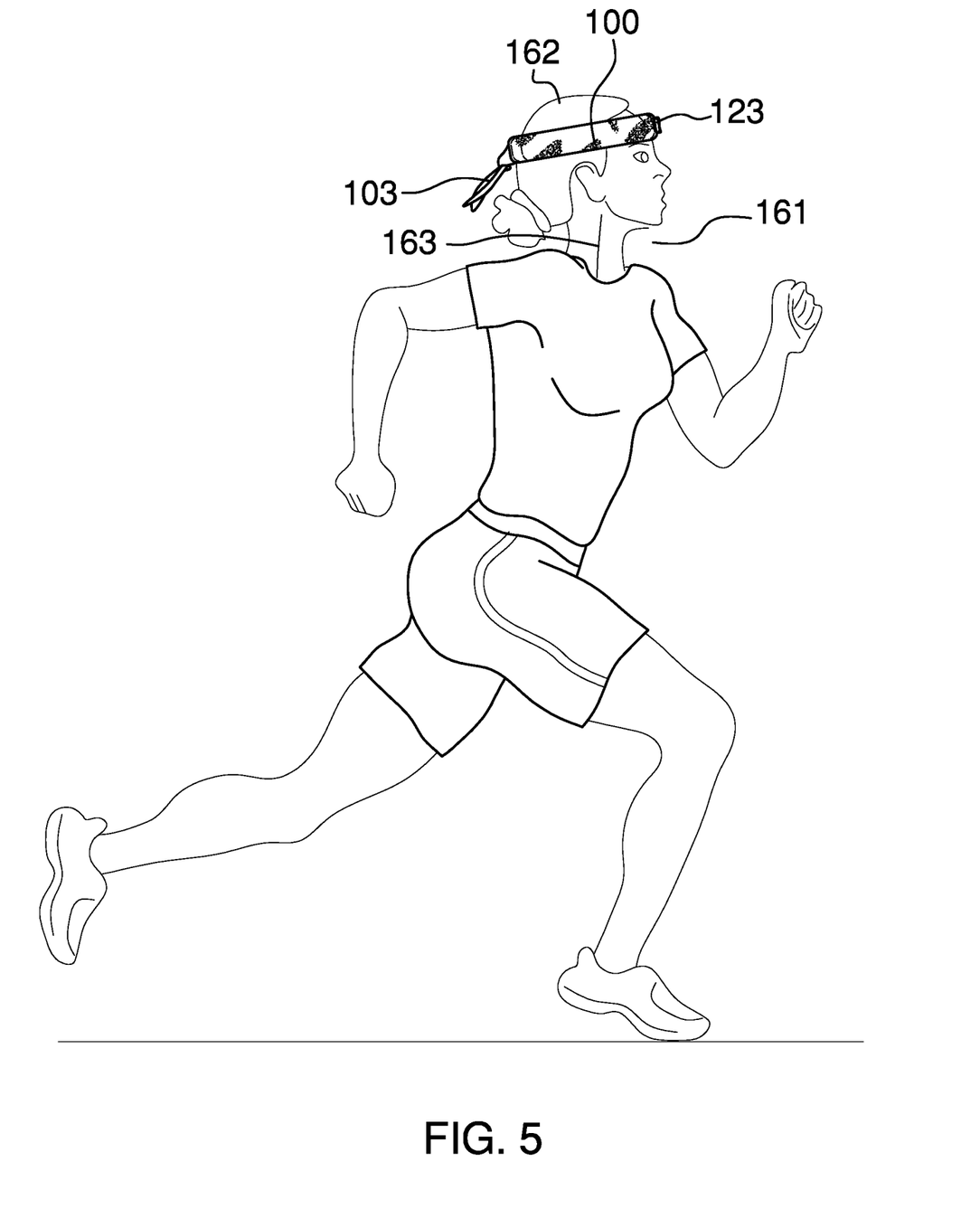
FIG. 5 is an in-use view of an embodiment of the disclosure.
Figure 6:
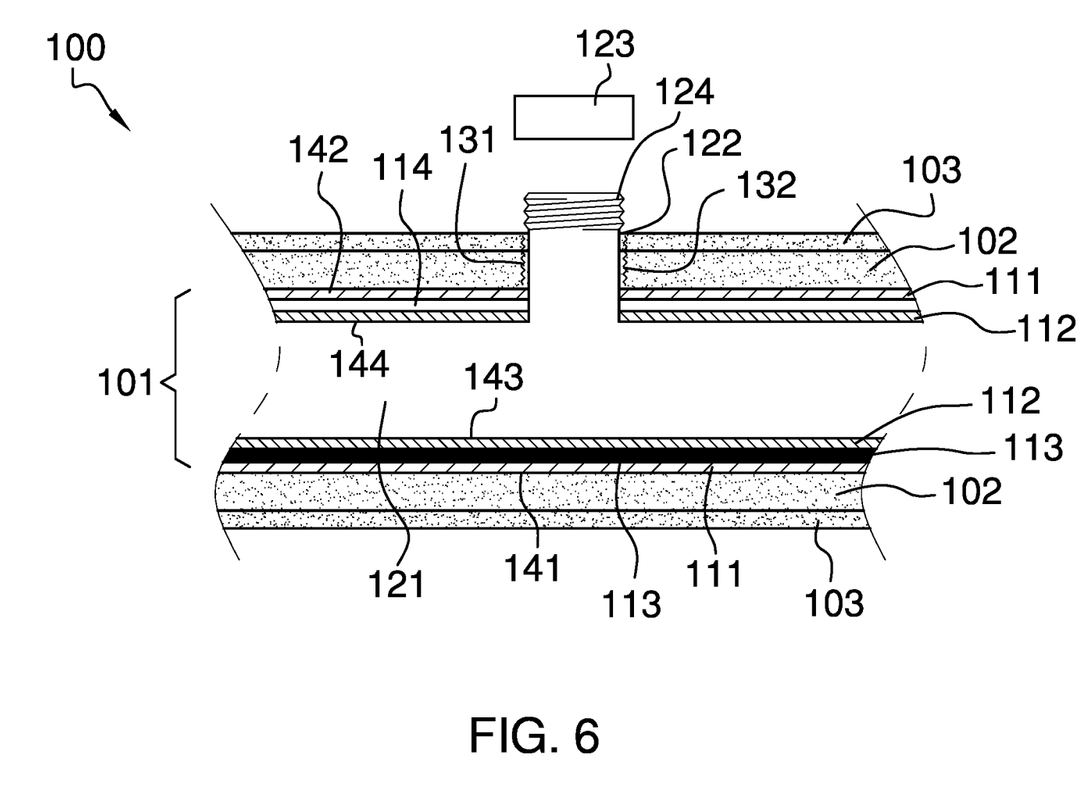
FIG. 6 is a detail view of an embodiment of the disclosure.

Optionally, the covering structure 103 may include a flap 777 that is used to cover the cap 123 when the invention 100 is in use (see FIGS. 1 and 5). The flap 777 is secured to the covering structure 103 via a stitching 778. A fastener 779 is provided on the covering structure 103 to temporarily secure the flap 777 over the cap 123. The fastener 779 maybe nylon hook and loop strips.

The following definitions were used in this disclosure:

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Cantilever: As used in this disclosure, a cantilever is a beam or other structure that projects away from an object and is supported on only one end. A cantilever is further defined with a fixed end and a free end. The fixed end is the end of the cantilever that is attached to the object. The free end is the end of the cantilever that is distal from the fixed end.

Cantilever V Spring: As used in this disclosure, a cantilever V spring is a torsion spring formed in a chevron, hyoid or horseshoe shape. The cantilever V spring comprises a first cantilever structure and a second cantilever structure wherein the fixed end of the first cantilever structure is attached to the fixed end of the second cantilever structure. Within this structure, when a force is applied to the cantilever V spring such that the first cantilever structure moves relative to from the second cantilever structure the force deforms the cantilever V spring in an elastic manner that: 1) resists the application of the force; and 2) stores the energy deformation such that when the force is no longer applied the cantilever V spring returns to its relaxed shape. Depending on the application, a cantilever V spring can be considered a torsion spring, a tension spring, or a compression spring.

Cap: As used in this disclosure, a cap is a protective cover that encloses a space.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Chamber: As used in this disclosure, a chamber is an enclosed or enclosable space that is dedicated to a purpose.

Concave: As used in this disclosure, concave is used to describe: 1) a surface that resembles the interior surface of a sphere; or, 2) a function with a curvature structure wherein a chord that connects any two points of the function will be lesser than (graphically below) or equal to the value of the function at any point along the chord.

Convex: As used in this disclosure, convex is used to describe: 1) a surface that resembles the outer surface of a sphere; or, 2) a function with a curvature structure wherein a chord that connects any two points of the function will be greater than (graphically above) or equal to the value of the function at any point along the chord.

Correspond: As used in this disclosure, the term correspond is used as a comparison between two or more objects wherein one or more properties shared by the two or more objects match, agree, or align within acceptable manufacturing tolerances.

Cushion: As used in this disclosure a cushion is a structure formed with a pad that is used to prevent injury or damage to a person or object.

Elastic: As used in this disclosure, an elastic is a material or object that deforms when a force is applied to it and that is able to return to its relaxed shape after the force is removed. A material that exhibits these qualities is also referred to as an elastomeric material.

Elastic Textile: As used in this disclosure, an elastic textile is a textile that contains elastic yarns as some of the yarns that make up the textile. An elastic textile is constructed such that the elastic textile will stretch when a force is applied and will return to its original shape when after the force is removed.

Flush: As used in this disclosure, the term flush is used to describe the alignment of a first surface and a second surface on a single plane.

Foam: As used in this disclosure, foam is a mass of gas-filled spaces, commonly referred to as bubbles, which are formed: 1) on or in a liquid or gel; or, 2) in a solid material.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1. Always use Correspond and One to One Horseshoe: As used in this disclosure, a horseshoe refers to the hyoid like shape of an object formed as a single structure with a continuous and smoothly curved shape. A horseshoe often has the shape of an open ring.

Hyoid: As used in this disclosure, a hyoid refers to a three-sided structure comprising a crossbeam, a first arm, and a second arm. In a hyoid, the first arm and the second arm project away from the crossbeam: 1) in the same direction; 2) at a roughly perpendicular angle to the crossbeam, and, 3) the span of the length of the first arm roughly equals the span of the length of the second arm. Hyoids generally have a U shaped appearance.

Inner Perimeter and Outer Perimeter: As used in this disclosure, the inner perimeter and the outer perimeter refer to two geometrically similar structures of a curved object. The inner perimeter refers to the geometrically similar structure with the shorter span. The outer perimeter refers to the geometrically similar structure with the greater span.

Insulating Structure: As used in this disclosure, an insulating structure is a structure that inhibits, and ideally prevents, the transfer of heat through the insulating structure. Insulating structures may also be used to inhibit or prevent the transfer of sound through the insulating structure. Methods to form insulating structures include, but are not limited to: 1) the use of materials with low thermal conductivity; and, 2) the use of a structural design that places a vacuum within the insulating structure within the anticipated transfer path of the heat or sound.

Negative Space: As used in this disclosure, negative space is a method of defining an object through the use of open or empty space as the definition of the object itself, or, through the use of open or empty space to describe the boundaries of an object.

One to One: When used in this disclosure, a one to one relationship means that a first element selected from a first set is in some manner connected to only one element of a second set. A one to one correspondence means that the one to one relationship exists both from the first set the second set and from the second set to the first set. A one to one fashion means that the one to one relationship exists in only one direction.

Port: As used in this disclosure, a port is an opening formed in an object that allows fluid to flow through the boundary of the object.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Radial: As used in this disclosure, the term radial refers to a direction that: 1) is perpendicular to an identified central axis; or, 2) projects away from a center point.

Relaxed Shape: As used in this disclosure, a structure is considered to be in its relaxed state when no shear, strain, or torsional forces are being applied to the structure.

Reservoir: As used in this disclosure, a reservoir refers to a container or containment system that is configured to store a liquid.

Semi-Rigid Structure: As used in this disclosure, a semi-rigid structure is a solid structure that is stiff but not wholly inflexible and that will deform under force before breaking. A semi-rigid structure may or may not behave in an elastic fashion in that a semi-rigid structure need not return to a relaxed shape.

Shell: As used in this disclosure, a shell is a structure that forms an outer covering intended to contain an object. Shells are often, but not necessarily, rigid or semi-rigid structures that are intended to protect the object contained within it.

Spring: As used in this disclosure, a spring is a device that is used to store mechanical energy. This mechanical energy will often be stored by: 1) deforming an elastomeric material that is used to make the device; 2) the application of a torque to a rigid structure; or 3) a combination of the previous two items.

Textile: As used in this disclosure, a textile is a material that is woven, knitted, braided or felted. Synonyms in common usage for this definition include fabric and cloth.

Threaded Connection: As used in this disclosure, a threaded connection is a type of fastener that is used to join a first tube-shaped and a second tube-shaped object together. The first tube-shaped object is fitted with a first fitting selected from an interior screw thread or an exterior screw thread. The second tube-shaped object is fitted with the remaining screw thread. The tube-shaped object fitted with the exterior screw thread is placed into the remaining tube-shaped object such that: 1) the interior screw thread and the exterior screw thread interconnect; and, 2) when the tube-shaped object fitted with the exterior screw thread is rotated the rotational motion is converted into linear motion that moves the tube-shaped object fitted with the exterior screw thread either into or out of the remaining tube-shaped object. The direction of linear motion is determined by the direction of rotation.

Tubular Textile: As used in this disclosure, a tubular textile is a textile that is woven, knitted, or braided into a seamless tube-like shape.

Vacuum: As used in this disclosure, a vacuum is used to describe a first space that contains gas at a reduced gas pressure relative to the gas pressure of a second space. If the first space and the second space are connected together, this pressure differential will cause gas from the second space to move towards the first space until the pressure differential is eliminated.

With respect to the above description, it is to be realized that the optimum dimensional relationship for the various components of the invention described above and in FIGS. 1 through 6 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A personal thermal control device comprising:
a heat transfer structure, a foam layer, and a covering structure;
wherein the foam layer is a cushion that covers the heat transfer structure;
wherein the heat transfer structure and the foam layer insert into the covering structure;
wherein the personal thermal control device is adapted for use with a person;
wherein the person is further defined with a head and a neck;

wherein the personal thermal control device is worn by the person;

wherein the personal thermal control device transfers heat to and from the person;

wherein the covering structure attaches the personal thermal control device to the person;

wherein the heat transfer structure comprises a shell, a reservoir, a joint, and a negative buffer;

wherein the shell contains the reservoir and the negative buffer;

wherein the joint joins the reservoir to the shell;

wherein the shell is further defined with a shell inner perimeter and a shell outer perimeter;

wherein the reservoir is further defined with a reservoir inner perimeter and a reservoir outer perimeter;

wherein the shell contains the reservoir such that the reservoir is located within the reduced pressure environment of the shell.

2. The personal thermal control device according to claim 1 wherein the heat transfer structure is an insulated structure;

wherein the heat transfer structure is a hollow horseshoe-shaped structure;

wherein the heat transfer structure transfers heat between the person and the personal thermal control device.

3. The personal thermal control device according to claim 2 wherein the heat transfer structure acts as a spring;

wherein the spring structure of the heat transfer structure binds the heat transfer structure to the head of the person.

4. The personal thermal control device according to claim 3 wherein the covering structure is a textile-based structure;

wherein the foam layer forms a cushion;

wherein the foam layer attaches to the exterior surfaces of the heat transfer structure.

5. The personal thermal control device according to claim 4 wherein the shell is a hollow semi-rigid structure;

wherein the semi-rigid structure of the shell has an elastic nature;

wherein the shell forms the exterior surface of the heat transfer structure;

wherein the shell has a horseshoe shape;

wherein the shell contains gas at a reduced pressure relative to the atmosphere.

6. The personal thermal control device according to claim 5 wherein the shell is formed from aluminum.

7. The personal thermal control device according to claim 6 wherein the reservoir is a hollow semi-rigid structure;

wherein the semi-rigid structure of the reservoir has an elastic nature;

wherein the reservoir forms a fluid impermeable space within the interior of the shell;

wherein the reservoir is geometrically similar to the shell.

8. The personal thermal control device according to claim 7 wherein the reservoir contains a heat transfer medium.

9. The personal thermal control device according to claim 8 wherein the reservoir inner perimeter of the reservoir is directly joined to the shell inner perimeter of the shell such that heat can transfer between the shell and the heat transfer medium contained within the reservoir;

wherein the reservoir is a gas impermeable structure that contains the heat transfer medium at a pressure that is different from the low-pressure gas contained within the shell.

10. The personal thermal control device according to claim 9 wherein the reservoir is formed from bronze.

11. The personal thermal control device according to claim 10 wherein the reservoir further comprises a chamber, a port, a cap, and a threaded connection;

wherein the hollow interior of the reservoir forms the chamber;

wherein the port attaches to the chamber;

wherein the cap attaches to the port;

wherein the threaded connection attaches the cap to the port.

12. The personal thermal control device according to claim 11 wherein the chamber is a fluid impermeable enclosed structure;

wherein the chamber forms the storage space within which the heat transfer medium is stored.

13. The personal thermal control device according to claim 12 wherein the port is a tubular structure that provides access to the chamber;

wherein the heat transfer medium is introduced into and removed from the chamber through the port;

wherein the port projects away from the chamber in a direction towards the shell outer perimeter of the shell.

14. The personal thermal control device according to claim 13 wherein the shell forms a brazed seal around the port as it passes through the shell outer perimeter.

15. The personal thermal control device according to claim 14 wherein the heat transfer medium is a fluid that is heated or cooled before being introduced into the chamber;

wherein the temperature of the heat transfer medium determines the direction of heat transfer during use of the personal thermal control device;

wherein the specific heat capacity of the selected heat transfer medium be greater than or equal the specific heat capacity of water.

16. The personal thermal control device according to claim 15 wherein the joint is a flux material that is used to braze the reservoir inner perimeter to the shell inner perimeter.

17. The personal thermal control device according to claim 16 wherein the negative buffer is a negative space formed between the shell outer perimeter of the shell and the reservoir outer perimeter of the reservoir;

wherein the reduced pressure gas is stored in the negative buffer;

wherein the reduced pressure gas in the negative buffer forms an insulating structure that inhibits heat transfer in a direction away from the person wearing the personal thermal control device.

18. The personal thermal control device according to claim 17 wherein the foam layer is a polyurethane foam;

wherein the covering structure is a tubular textile;

wherein the foam layer further comprises an inner cap aperture;

wherein the inner cap aperture allows the port to pass through the foam layer;

wherein the covering structure is an elastic textile;

wherein the covering structure further comprises an outer cap aperture;
wherein the outer cap aperture allows the port to pass through the covering structure;
wherein the covering structure includes a flap that is used to cover the cap when the personal thermal control device is in use;
wherein the flap is secured to the covering structure via a stitching;
wherein a fastener is provided on the covering structure to temporarily secure the flap over the cap.

* * * * *